US007542540B2

(12) United States Patent
Matsuda

(10) Patent No.: US 7,542,540 B2
(45) Date of Patent: Jun. 2, 2009

(54) X-RAY CT APPARATUS

(75) Inventor: Keiji Matsuda, Nasushiobara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 30 days.

(21) Appl. No.: 11/456,682

(22) Filed: Jul. 11, 2006

(65) Prior Publication Data

US 2007/0025498 A1 Feb. 1, 2007

(30) Foreign Application Priority Data

Jul. 15, 2005 (JP) ............... 2005-206873

(51) Int. Cl.
*A61B 6/03* (2006.01)
(52) U.S. Cl. ............................................. 378/7
(58) Field of Classification Search ............... 378/7, 378/9
See application file for complete search history.

(56) References Cited

U.S. PATENT DOCUMENTS

| 5,815,546 | A * | 9/1998 | Flohr et al. ............... 378/4 |
| 6,173,033 | B1 | 1/2001 | Klingenbeck-Regn et al. |
| 6,421,412 | B1 | 7/2002 | Hsieh et al. |
| 2003/0031290 | A1* | 2/2003 | Sugihara et al. ............ 378/15 |
| 2004/0034269 | A1 | 2/2004 | Ozaki |
| 2004/0114710 | A1 | 6/2004 | Ozaki |
| 2004/0213371 | A1 | 10/2004 | Bruder et al. |
| 2004/0247070 | A1* | 12/2004 | Ali et al. ..................... 378/4 |
| 2005/0053188 | A1 | 3/2005 | Gohno |
| 2006/0083351 | A1* | 4/2006 | Lamberty et al. ............ 378/86 |

FOREIGN PATENT DOCUMENTS

| JP | 2000-197628 | 7/2000 |
| JP | 2002-172112 | 6/2002 |
| JP | 2004-73406 | 3/2004 |
| WO | WO 2006/056915 A1 | 6/2006 |

OTHER PUBLICATIONS

Translation of JP 2000-197628 A dated Jul. 18, 2000.*

* cited by examiner

*Primary Examiner*—Chih-Cheng G Kao
(74) *Attorney, Agent, or Firm*—Oblon, Spivak, McClelland, Maier & Neustadt, P.C.

(57) ABSTRACT

An X-ray CT apparatus includes X-ray tubes, slit mechanisms which are respectively provided for X-ray tubes and whose slit widths can be changed, two-dimensional array type X-ray detectors which form pairs with the X-ray tubes, a support mechanism which supports the X-ray tubes and the X-ray detectors so as to allow them to rotate about a rotation axis parallel to the slice direction, a correction unit which corrects data from each detection element located in an area which X-rays passing through the slit mechanism directly strike, by using data from at least one detection element located outside the area and associated with the same channel in order to reduce a scattered radiation component originating from X-rays generated by an X-ray tube other than the X-ray tube forming the pair, and a reconstruction unit which reconstructs image data on the basis of the corrected data.

9 Claims, 7 Drawing Sheets

X-RAY CT APPARATUS

CROSS-REFERENCE TO RELATED APPLICATIONS

This application is based upon and claims the benefit of priority from prior Japanese Patent Application No. 2005-206873, filed Jul. 15, 2005, the entire contents of which are incorporated herein by reference.

BACKGROUND OF THE INVENTION

1. Field of the Invention

The present invention relates to a multi-tube type X-ray computed tomography (CT) apparatus comprising a plurality of pairs of X-ray tubes and detectors.

2. Description of the Related Art

Conventionally, an X-ray CT apparatus is designed to apply X-rays generated by an X-ray tube to a subject to be examined and detect X-rays transmitted through the subject by using an X-ray detector, thereby obtaining a tomogram by performing reconstruction processing for detected data using a computer. A multi-tube type X-ray CT apparatus is also known, in which two or more pairs of X-ray tubes and detectors are mounted on an annular rotating frame to reduce the rotation angle of the frame.

A multi-tube type X-ray CT apparatus is disclosed in, for example, Jpn. Pat. Appln. KOKAI Publication No. 2004-73406. This reference shows an apparatus which includes an X-ray tube for medical treatment and an X-ray tube for visualization. In a multi-tube type X-ray CT apparatus on which two or more pairs of X-ray tubes and detectors are mounted, direct radiation from the X-ray tube of a given pair and scattered radiation from the X-ray tube of another pair may reach the detector of the given pair. In addition, since direct radiation does not differ much in characteristics from scattered radiation, it is difficult to separate them. For this reason, the image quality of a reconstructed image is affected by scattered radiation from the X-ray tube of a pair other than the given pair.

Conventionally, in a multi-tube type X-ray CT apparatus on which two or more pairs of X-ray tubes and X-ray detectors are mounted, scattered radiation from the X-ray tube of a pair other than a given pair affects the image quality of a reconstructed image.

BRIEF SUMMARY OF THE INVENTION

It is an object of the present invention to reduce the influence of scattered radiation originating from X-rays from the X-ray tube of the other pair in an multi-tube type X-ray CT apparatus including a plurality of pairs of X-ray tubes and detectors.

According to a first aspect of the present invention, there is provided an X-ray CT apparatus comprising a plurality of X-ray tubes, a plurality of slit mechanisms which are respectively provided for the plurality of X-ray tubes and whose slit widths are adapted to be changed, a plurality of X-ray detectors which form pairs with the plurality of X-ray tubes, each X-ray detector including a plurality of detection elements arrayed in a matrix form in a channel direction and a slice direction, a support mechanism which supports the X-ray tubes and the X-ray detectors so as to allow the X-ray tubes and the X-ray detectors to rotate about a rotation axis parallel to the slice direction, a correction unit which corrects data from each detection element located in an area which X-rays passing through the slit mechanism directly strike, by using data from at least one detection element located outside the area and associated with the same channel in order to reduce a scattered radiation component originating from X-rays generated by an X-ray tube other than the X-ray tube forming the pair, and a reconstruction unit which reconstructs image data on the basis of the corrected data.

According to a second aspect of the present invention, there is provided an X-ray CT apparatus comprising a plurality of X-ray tubes, a plurality of slit mechanisms which are respectively provided for the plurality of X-ray tubes and whose slit widths are adapted to be changed, a plurality of X-ray detectors which form pairs with the plurality of X-ray tubes, each X-ray detector including a plurality of detection elements arrayed in a matrix form in a channel direction and a slice direction, a support mechanism which supports the X-ray tubes and the X-ray detectors so as to allow the X-ray tubes and the X-ray detectors to rotate about a rotation axis parallel to the slice direction, a correction unit which corrects projection data from each detection element located in an area which X-rays passing through the slit mechanism directly strike, by using scattered radiation data from at least one detection element located outside the area and associated with the same channel, and a reconstruction unit which reconstructs image data on the basis of projection data which has not undergone the correction in a first mode of performing data acquisition by using a single pair of the plurality of pairs, and reconstructs image data on the basis of projection data which has undergone the correction in a second mode of performing data acquisition by using the plurality of pairs.

According to a third aspect of the present invention, there is provided an X-ray CT apparatus comprising a plurality of X-ray tubes, a plurality of slit mechanisms which are respectively provided for the plurality of X-ray tubes and whose slit widths are adapted to be changed, a plurality of X-ray detectors which form pairs with the plurality of X-ray tubes, each X-ray detector including a plurality of detection elements arrayed in a matrix form in a channel direction and a slice direction, a support mechanism which supports the X-ray tubes and the X-ray detectors so as to allow the X-ray tubes and the X-ray detectors to rotate about a rotation axis parallel to the slice direction, a setting support unit which supports setting of a scan condition by preparing a plurality of candidates associated with combinations of imaging slice thicknesses and imaging slice counts which correspond to an entire effective area of the X-ray detector in a first mode of performing data acquisition by using a single pair of the plurality of pairs, and by preparing a plurality of candidates corresponding to part of an effective area from which at least detection elements of the X-ray detector which are located on two end rows are excepted, in a second mode of performing data acquisition by using the plurality of pairs, a control unit which controls the slit mechanism in accordance with a combination of an imaging slice thickness and an imaging slice count which is selected in accordance with a user instruction, a correction unit which corrects data from each detection element located in part of the effective area which X-rays passing through the slit mechanism directly strike, by using data from at least one detection element located outside the part and associated with the same channel, and a reconstruction unit which reconstructs image data on the basis of data which has undergone the correction in the second mode, and reconstructs image data on the basis of data which has not undergone the correction in the first mode.

According to a fourth aspect of the present invention, there is provided an X-ray CT apparatus comprising a plurality of X-ray tubes, a plurality of slit mechanisms which are respectively provided for the plurality of X-ray tubes and whose slit widths are adapted to be changed, a plurality of X-ray detectors which form pairs with the plurality of X-ray tubes, each X-ray detector including a plurality of detection elements arrayed in a matrix form in a channel direction and a slice direction, a support mechanism which supports the X-ray tubes and the X-ray detectors so as to allow the X-ray tubes and the X-ray detectors to rotate about a rotation axis parallel to the slice direction, a control unit which controls the slit mechanism to apply X-rays to an entire effective area of the X-ray detector in a first mode of performing data acquisition by using a single pair of the plurality of pairs, and controls the slit mechanism to apply X-rays to part of an effective area of the X-ray detector from which at least two end rows are excepted, in a second mode of performing data acquisition by using the plurality of pairs, a correction unit which corrects data from each detection element located in the part which X-rays passing through the slit mechanism directly strike, by using data from at least one detection element located outside the area and associated with the same channel, and a reconstruction unit which reconstructs image data on the basis of data which has undergone the correction in the second mode, and reconstructs image data on the basis of data which has not undergone the correction in the first mode.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out herein after.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment of the present invention will be described below in detail with reference to the views of the accompanying drawing.

Figure 1:
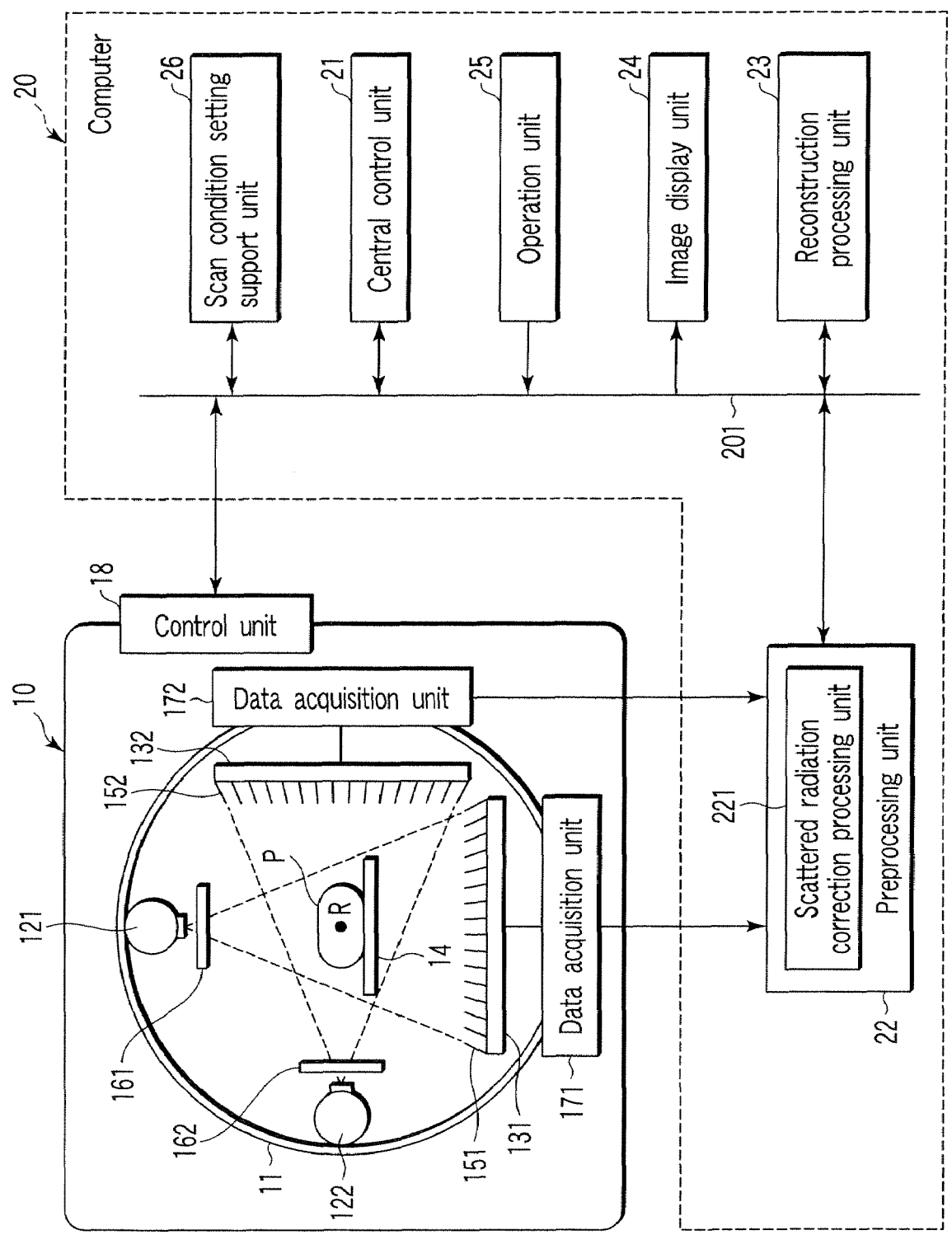
FIG. 1 is a block diagram showing the overall arrangement of an X-ray CT apparatus according to an embodiment of the present invention.

FIG. 1 is a block diagram showing the overall arrangement of an X-ray CT apparatus according to an embodiment of the present invention. Referring to FIG. 1, the X-ray CT apparatus (X-ray computed tomography apparatus) of this embodiment includes a gantry 10, a computer 20, and a bed (not shown). The gantry 10 is of a multi-tube type, on which a plurality of pairs of X-ray tubes and X-ray detectors are mounted. In this embodiment, this gantry will be described as a two-tube type gantry.

The gantry 10 is provided with a rotating frame 11. The rotating frame 11 rotates about a rotation axis R by a rotating mechanism (not shown). The first pair of an X-ray tube 121 and an X-ray detector 131 and the second pair of an X-ray tube 122 and an X-ray detector 132 are mounted on the rotating frame 11. The imaging axis of the first pair intersects the imaging axis of the second pair typically at 90°. Each imaging axis is a line connecting the X-ray focal point and the detector center. An opening portion is formed in the central portion of the rotating frame 11. A subject P placed on a top 14 of the bed is inserted into the opening portion.

The X-ray detectors 131 and 132 are respectively provided with collimators 151 and 152 which face the X-ray tubes 121 and 122 to focus X-rays. Slit mechanisms 161 and 162 are arranged at the X-ray tubes 121 and 122. Each of the slit mechanisms 161 and 162 includes at least two lead slit plates. The slit plates are supported to be movable parallel to a rotation axis R so as to adjust the width of the slit between the two slit plates. An X-ray thickness is determined by a slit width.

Outputs from the X-ray detectors 131 and 132 are sent to data acquisition units 171 and 172 and supplied to a preprocessing unit (to be described later) of the computer 20. The gantry 10 is also provided with a control unit 18, which performs control on the tube voltages of the X-ray tubes 121 and 122, rotation control on the rotating frame 11, and the like.

The computer 20 includes a central control unit 21, to which a preprocessing unit 22, reconstruction processing unit 23, image display unit 24, operation unit 25, and the like are connected through a data/control bus line 201. X-rays transmitted through the subject P are converted into electrical signals by the X-ray detectors 131 and 132, and are amplified and converted into digital data by the data acquisition units 171 and 172. The projection data are then supplied to the preprocessing unit 22. The preprocessing unit 22 performs processing such as correction of signal intensities and correction of signal omissions. The preprocessing unit 22 includes a scattered radiation correction processing unit 221 to reduce the influence of scattered radiation mainly originating from X-rays generated by the X-ray tube of the other pair, and outputs the imaging data processed by the preprocessing unit 22 onto the bus line 201.

The central control unit 21 controls the operation of each unit of the computer 20 and controls the control unit 18 of the gantry 10. The reconstruction processing unit 23 reconstructs tomogram data on the basis of projection data. The image display unit 24 includes a display which displays medical images and the like. The operation unit 25 is used by a doctor to input information such as the state of a patient, an examination method, and the like.

Figure 2:
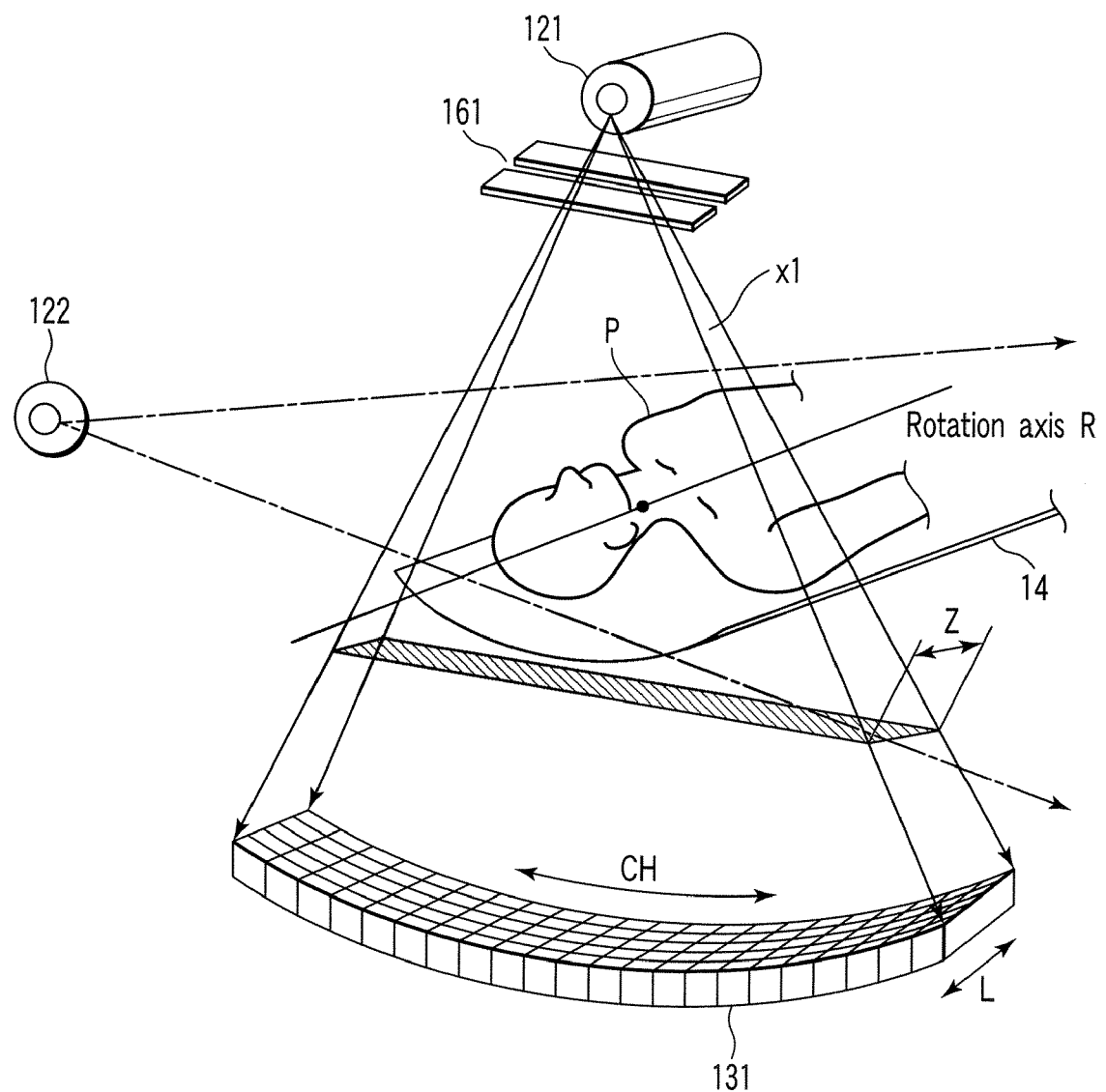
FIG. 2 is a perspective view showing the arrangement of the main part of the X-ray CT apparatus according to the embodiment.

FIG. 2 is an enlarged view of the arrangements of the X-ray tubes 121 and 122 and X-ray detectors 131 and 132, i.e., the arrangement of the first pair of the X-ray tube 121 and the X-ray detector 131, and the arrangement of the second pair of the X-ray tube 122 and the X-ray detector 132. FIG. 2 representatively shows the first pair of the X-ray tube 121 and the X-ray detector 131. The second pair of the X-ray tube 122 and the X-ray detector 132 has the same arrangement as that of the first pair except that the second pair is shifted from the first pair by an angle of 90°, and hence an illustration of the second pair will be omitted in FIG. 2.

Referring to FIG. 2, the slit mechanism 161 is placed to face the X-ray tube 121. An X-ray thickness Z is determined by the slit mechanism 161. The X-ray detector 131 includes many detection elements arrayed in the channel direction (CH) and the slice direction (L), and detects an incident X-ray beam x1.

The X-ray detector 131 is provided with the metal plate collimator 151 (see FIG. 1) in the channel (CH) direction, and is designed to receive X-rays from the direction of the X-ray tube belonging to the same pair. The multi-tube type X-ray CT apparatus is smaller in rotation angle than a single tube type apparatus, and can shorten the time required to acquire projection data, and hence can improve the time resolution.

The X-ray detectors 131 and 132 are designed to detect X-rays (direct radiation) from the X-ray tubes 121 and 122 of the corresponding pairs and scattered radiation from the X-ray tubes of the other pairs with detection elements in middle portions L0 in the slice direction and also detect scattered radiation from the X-ray tubes of the other pairs with detection elements located outside areas L1 and L2 of the respective arrays.

Figure 3:
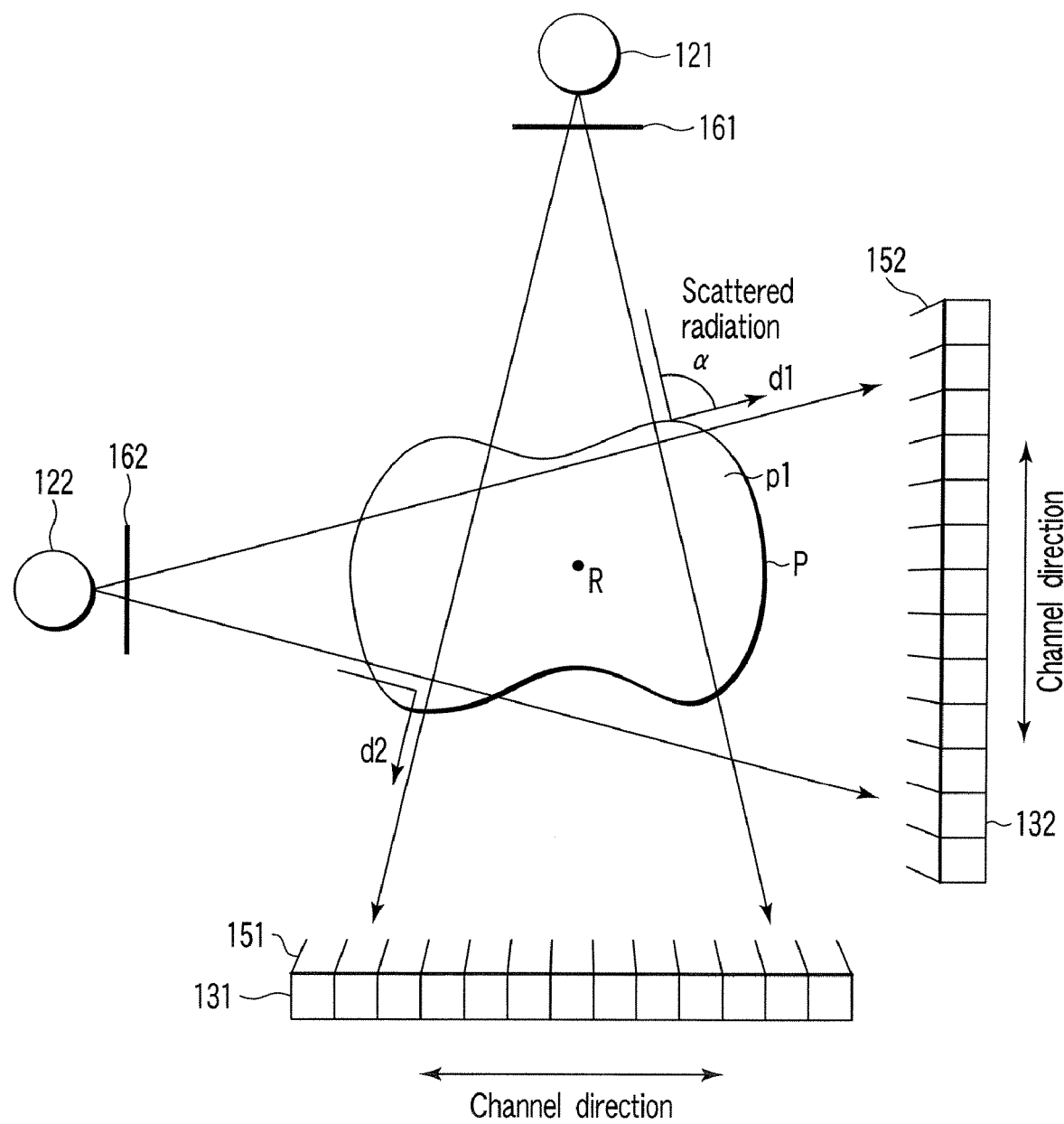
FIG. 3 is a view for explaining the influence of scattered radiation in the X-ray CT apparatus in the embodiment.

FIG. 3 is a view for explaining the influence of scattered radiation from an X-ray tube of a pair other than a given pair. In the case shown in FIG. 3, X-rays emitted from the X-ray tube 121 are detected by the X-ray detector 131, and X-rays emitted from the X-ray tube 122 are detected by the X-ray detector 132.

Figure 4:
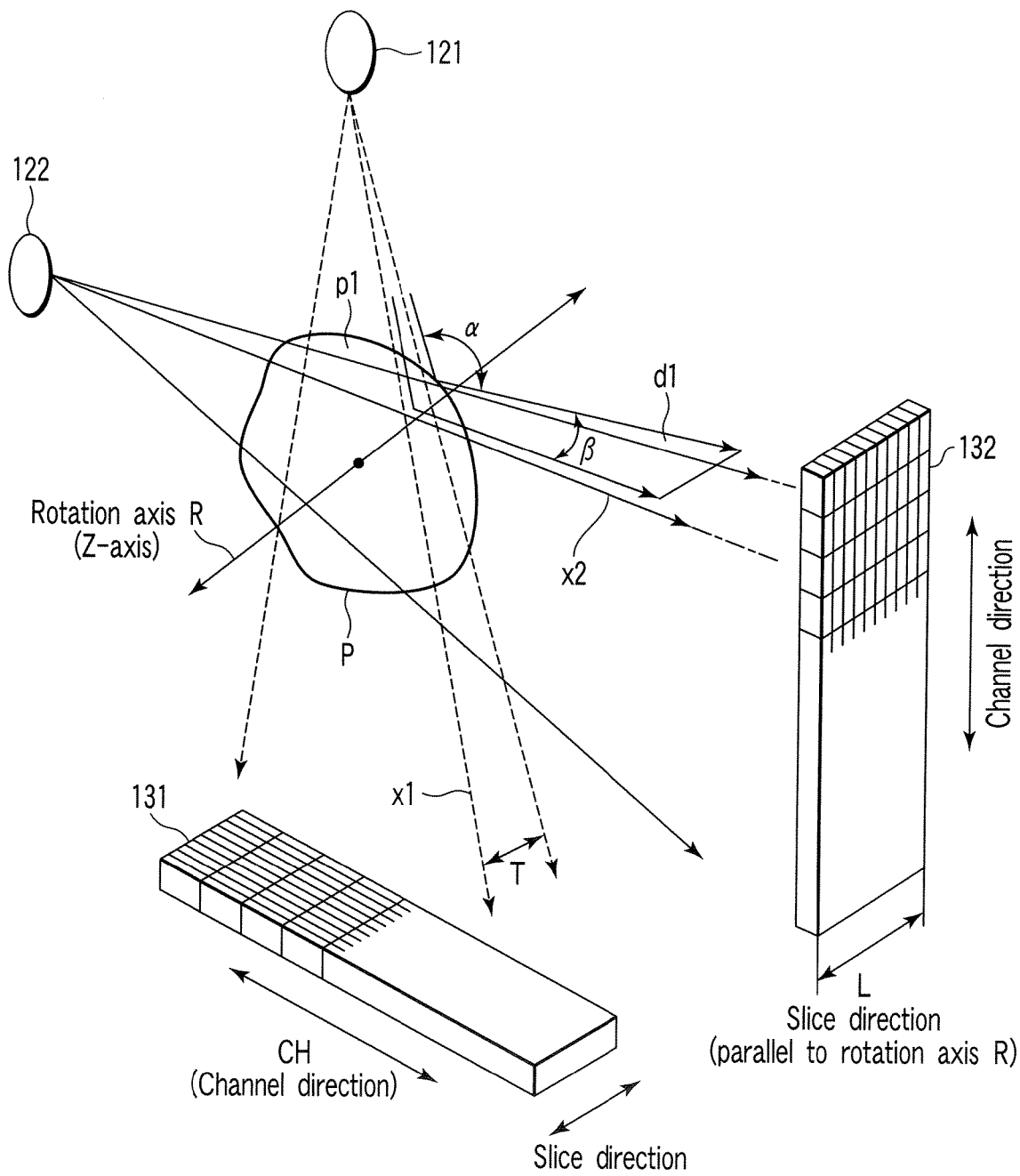
FIG. 4 is a view for schematically explaining a state wherein scattered radiation occurs in the X-ray CT apparatus

X-rays from the X-ray tube 121 of the other pair are scattered by the surface and an interior p1 of the subject P and strike the X-ray detector 132. Likewise, X-rays from the X-ray tube 122 of the other pair are scattered by the surface and interior p1 of the subject P and strike the X-ray detector 131. Scattered radiation at the subject P is radially scattered, and is mostly blocked by the collimators 151 and 152. Some of the scattered radiation (e.g., d1 and d2) pass through the collimators 151 and 152 and strike the detectors 131 and 132. The scattered radiation d1 scattered at a scattering angle α is X-rays from the X-ray tube 121 which strike and are scattered by the interior p1 of the subject P. This radiation is scattered at a refraction angle α of about 90° and strikes the X-ray detector 132. The scattered radiation d2 is X-rays from the X-ray tube 122 which strike and are scattered by the interior p1 of the subject P. This radiation is scattered at the refraction angle α of about 90° and strikes the X-ray detector 131. Note that X-rays generated by the X-ray tube 122 (121) of the other pair which are scattered by the body surface of the subject P and are directly detected as scattered radiation by the detector 131 (132) without being attenuated have the worst effect. The manner of how scattered radiation occurs will be more specifically described with reference to FIG. 4. FIG. 4 schematically shows how X-rays from the X-ray tube 121 are scattered by the interior p1 of the subject and strike the X-ray detector 132 of the other pair.

An X-ray beam x2 (direct radiation) from the X-ray tube 122 of one pair strikes the X-ray detector 132. However, when an X-ray beam from the X-ray tube 121 of the other pair strikes the interior p1 of the subject, the X-ray beam is scattered at the refraction angle α to produce the scattered radiation d1. The scattered radiation d1 is also scattered and spread in the slice direction (L) of the X-ray detector 132, and strikes the X-ray detector 132 with a spread angle of about 5° to 6° as indicated by an angle β.

Since α≫β, the scattered radiation d1 sufficiently isotropically (uniformly) strikes detection element arrays on the same channels of the X-ray detectors 131 and 132 from one end to the other end. Since the X-ray beam x1 has a predetermined slice thickness (T), the scattering point is thought to correspond to the slice thickness, and the amount of scattered radiation is an integral value at this scattering point. Even if, therefore, there is a point at which X-rays are scattered strongly in a specific direction, since scattered radiation from one end to the other end of the detection element in the slice direction is integrated, the specificity is reduced. As a consequence, the distribution of scattered radiation intensities in the slice direction becomes uniform.

Figure 5:
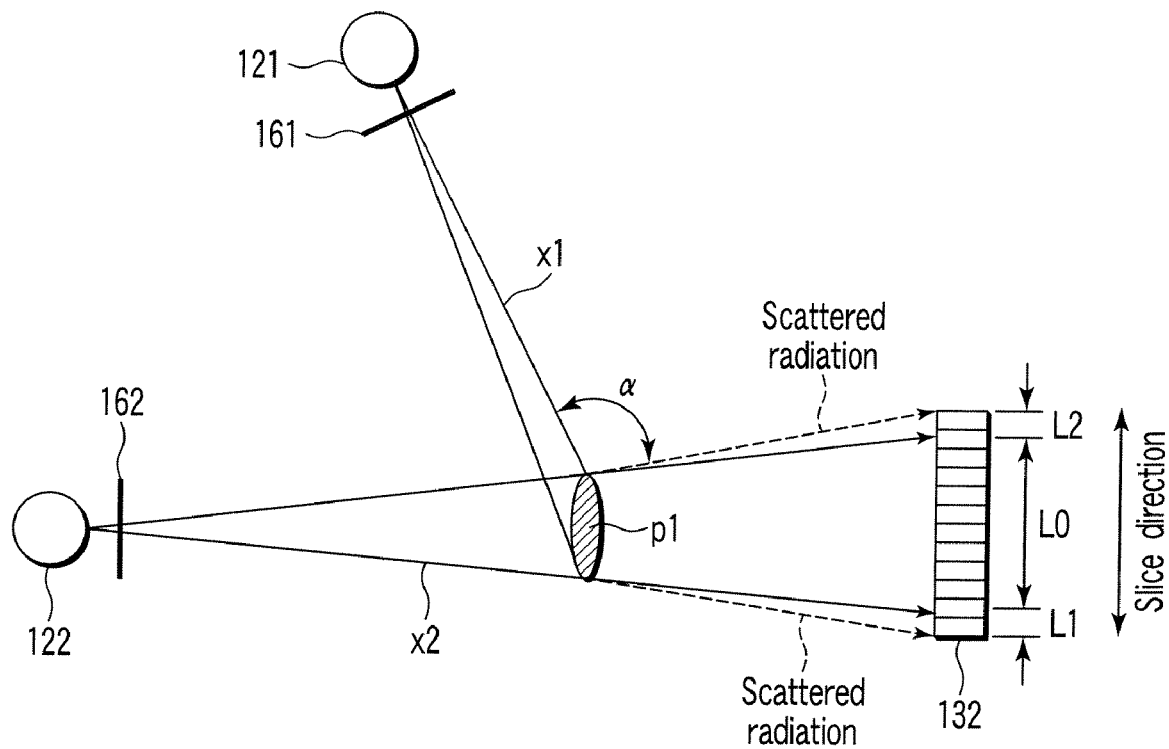
FIG. 5 is a view for explaining the occurrence of scattered radiation in the X-ray CT apparatus when viewed from the slice direction of the X-ray detector.

In addition, only scattered radiation strikes the detection elements located at the two end portions of each of the detectors 131 and 132 in the slice direction, but no direct radiation from the X-ray tubes 121 and 122 strikes them. This phenomenon will be described with reference to FIG. 5. FIG. 5 is a view showing how the scattered radiation d1 is applied to the X-ray detector 132. This is a sectional view of the X-ray detector 132 in the slice direction with a scattered radiation source being represented by P1. As is obvious from FIG. 5, the X-ray beam x2 (direct radiation) from the X-ray tube 122 and scattered radiation d1 strike the middle area L0 of the X-ray detector 132 in the slice direction. On the other hand, only the scattered radiation d1 strikes the two end areas L1 and L2 in the slice direction. Therefore, the detection elements in the areas L1 and L2 can measure only scattered radiation of X-rays.

In this embodiment, when X-rays applied through the slits of the slit mechanisms 161 and 162 are detected by the detectors 131 and 132, the detection elements in the two end areas L1 and L2 in the slice direction are used to measure scattered radiation. The influence of scattered radiation can be reduced by subtracting the measured amount of X-rays by the detection elements on the two end portions on the same channel from the measured amount of X-rays by the detection elements at the middle portion on the same channel on the basis of the fact that the amount of scattered radiation in the middle area L0 in the slice direction does not differ much from that in the outside areas L1 and L2.

That is, correction is made to reduce the influence of scattered radiation by using X-ray data detected by the detection elements in the outside areas L1 and L2 of the X-ray detectors 131 and 132 in the slice direction. This correction is performed by the scattered radiation correction processing unit 221 of the preprocessing unit 22. The scattered radiation correction processing unit 221 calculates scattered radiation data by integrating X-ray data detected by the elements in the outside areas L1 and L2 with the numbers of elements in the arrays, and subtracts the value of the scattered radiation data from the value of X-ray data detected by the elements in the middle areas L0 of the X-ray detectors 131 and 132 in the slice direction. The scattered radiation correction processing unit 221 then obtains imaging data on the basis of the result of the above processing and outputs the data onto the bus line 201.

Figure 6:
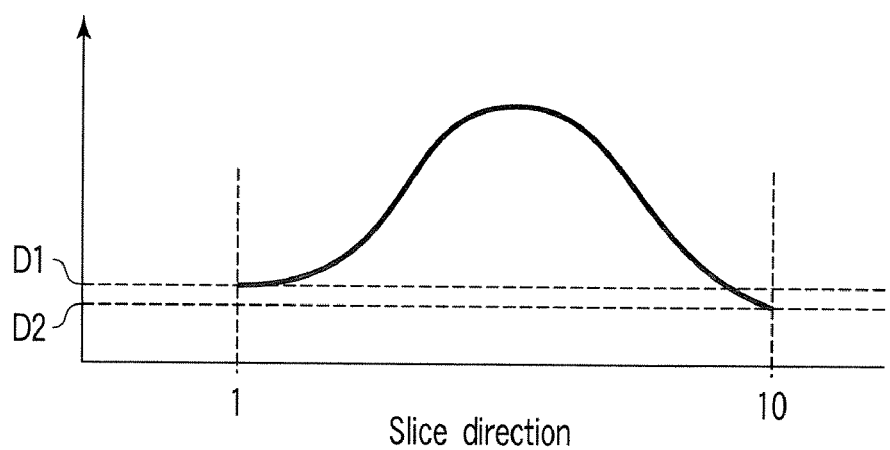
FIG. 6 is a graph for explaining the operation of a scattered radiation correction processing unit in the embodiment.

FIG. 6 is a graph for explaining the operation of the scattered radiation correction processing unit 221. Referring to FIG. 6, the ordinate represents the data value obtained by each of the X-ray detectors 131 and 132; and the abscissa, the slice number of each of the X-ray detectors 131 and 132. Data values associated with scattered radiation components detected by the detection elements in the outside areas L1 and L2 of the X-ray application area are subtracted from data values from the detection elements in the X-ray application areas L0 which are obtained from the values of the direct radiation of X-rays detected in the middle areas L0 of the X-ray detectors 131 and 132.

The width of each of the X-ray detectors 131 and 132 in the slice direction needs to be slightly larger than the maximum set value of the slice thickness (T) of an X-ray beam which is defined by the width of the slit mechanism 162. When the slit is reduced, scattered radiation can be measured with high accuracy by using the areas L1 and L2 for the measurement of scattered radiation which are located immediately outside the middle area L0 on the same channel which direct radiation strikes.

Figure 7:
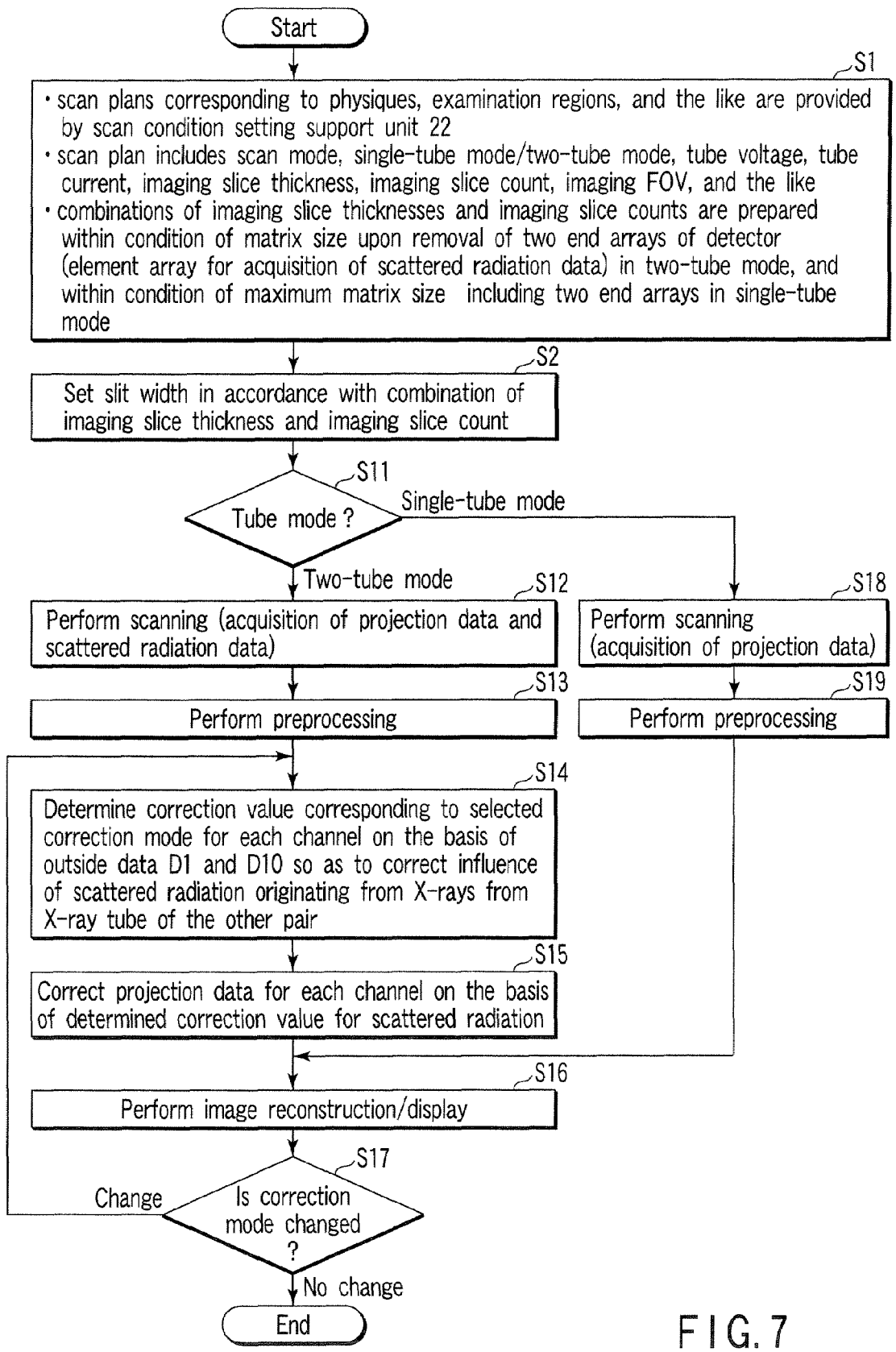
FIG. 7 is a flowchart showing the flow of processing from scan condition setting to image reconstruction in the embodiment.

Scattered radiation correction in this embodiment will be described in more detail. As shown in FIG. 7, scan conditions are set before scanning, box S1. A scan condition setting support unit 26 is provided to support a user to set scan conditions. The scan condition setting support unit 26 provides a plurality of scan plans corresponding to the physiques of subjects, examination regions, and the like. Each scan plan includes a scan mode (single/helical), differentiation between a single-tube scanning mode and a two-tube scanning mode, a tube voltage, a tube current, an imaging slice thickness, an imaging slice count, an imaging FOV, and the like. In this apparatus, one of the following modes can be selected: the single-tube mode of performing data acquisition (scanning) by using only one of the pairs while setting the other pair at a standstill, and the two-tube mode of performing data acquisition by using the two pairs.

A slit width is determined in box S2 by a combination of an imaging slice thickness and an imaging slice count. With this operation, the X-ray application area on the effective sensitivity area of each of the X-ray detectors 131 and 132 to which X-rays are to be applied is limited to the width defined by (imaging slice thickness)×(imaging slice count). In the two-tube mode, a plurality of candidates associated with combinations of imaging slice thicknesses and imaging slice counts are prepared within the maximum range which is the area set by excepting the two end rows of each of the X-ray detectors 131 and 132, which are used for the acquisition of scattered radiation data, from the effective sensitivity area unique to each of the X-ray detectors 131 and 132. In the single-tube mode, since no scattered radiation correction is performed, a plurality of candidates associated with combinations of imaging slice thicknesses and imaging slice counts are prepared within the entire effective sensitivity area unique to each of the X-ray detectors 131 and 132 as the maximum range (see box S11).

The user operates the operation unit 25 to select a desired combination from the plurality of candidates associated with the combinations of imaging slice thicknesses and imaging slice counts provided from the scan condition setting support unit 26. In order to apply X-rays to only the areas corresponding to the selected combination of the imaging slice thickness and the imaging slice count, the central control unit 21 adjusts the slit width by controlling the slit mechanisms 161 and 162. In the single-tube mode, X-rays may be applied to the entire effective sensitivity areas unique to the X-ray detectors 131 and 132.

Figure 8:
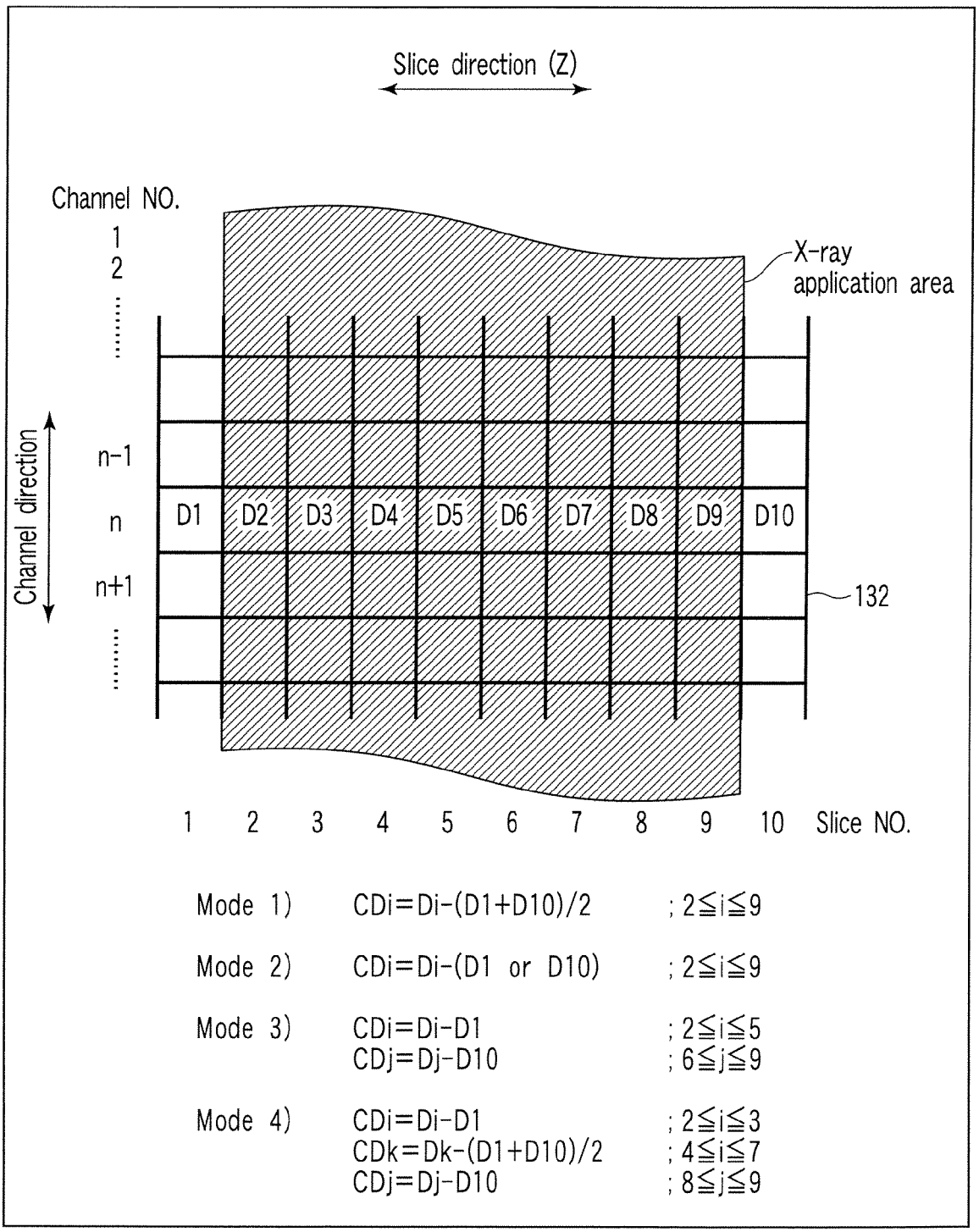
FIG. 8 is a view for supplementarily explaining step S15 in FIG. 7.

In the single-tube mode, since no scattered radiation correction is performed, X-rays can be applied to the entire area. In the two-tube mode, there is no chance that X-rays will be applied to the entire areas. In the two-tube mode, the maximum application area is the area obtained by excepting the two end rows from the entire area, as shown in FIG. 8. This is because, in the two-tube mode, the data obtained by the detection elements on the two end rows are used as scattered radiation correction data.

FIG. 8 illustrates ten rows type. However the type of four rows or more is applicable in this embodiment.

Obviously, in the single-tube mode, there is no chance that scattered radiation will originate from X-rays from the X-ray tube of the other pair. In the single-tube mode, since no scattered radiation correction is performed, an unwanted decrease in signal-noise ratio (SNR) can be prevented.

When the scan trigger button on the operation unit 25 is pressed by the user, scanning is started.

The central control unit 21 prepares different processing sequences for the single-tube mode and the two-tube mode. In the single-tube mode, since no scattered radiation correction is performed, the central control unit 21 acquires only data from the detection elements in the X-ray application area, i.e., only projection data which are transmitted through the subject and required for image reconstruction by scanning in step S18, and performs preprocessing for the acquired data (step S19). To acquire only the projection data is typically defined to store only the projection data without storing any data from the detection elements in X-ray non-application areas outside the X-ray application area.

In the two-tube mode, in the scanning operation in step S12, the central control unit 21 acquires both projection data from the detection elements in the X-ray application area and data from the detection elements (also called scattered radiation data or outside data) in the X-ray non-application areas of the two end rows outside the application area. The outside data is subjected to preprocessing equivalent to that for projection data (step S13). For example, in the case shown in FIG. 8, data D1 and D10 from the detection elements outside the X-ray application area are outside data, and data D2 to D9 from the detection elements in the X-ray application area are inside data (projection data).

The scattered radiation correction processing unit 221 corrects the inside data from the respective detection elements located in the X-ray application areas to which X-rays passing through the slits of the slit mechanisms 161 and 162 are directly applied by using the outside data from the detection elements which are located outside the X-ray application areas and are associated with the same channels as those of the data as correction targets (steps S14 and S15). In performing correction, the scattered radiation correction processing unit 221 determines a correction value for each channel from outside data in accordance with a correction mode. For the sake of descriptive convenience, assume that outside data are data D1 and D10 and inside data are data D2 to D9, as in the case shown in FIG. 8. Consider a channel n. The values of the inside data D2 to D9 are corrected by using the correction value determined from the outside data D1 and D10.

In correction mode 1), which is initially set, the average of the outside data D1 and S10 on the two ends is determined as a correction value.

In correction mode 2), one of the outside data D1 and D10 is determined as a correction value. For example, one of the maximum value and minimum value of the outside data D1 and D10 or a value approximate to a predetermined value is determined as a correction value for the channel n.

In correction mode 3), the outside data D1 from adjacent elements is assigned as a correction value for the inside data D2 to D5, and the outside data D10 from adjacent elements is assigned as a correction value for the inside data D6 to D9.

In correction mode 4), the outside data D1 from the adjacent elements is assigned as a correction value for the inside data D2 and D3, and the outside data D10 from the adjacent elements is assigned as a correction value for the inside data D8 and D9. As a correction value for the inside data D4 to D7 from the central portion, the average of the outside data D1 and D10 is determined.

Each of the values of the inside data D2 to D9 is corrected on the basis of the correction value determined in step S14 (step S15).

In the two-tube mode, the reconstruction processing unit 23 reconstructs image data on the basis of the inside data (projection data) corrected in step S15 under the control of the central control unit 21. In the single-tube mode, image data is reconstructed on the basis of projection data which has not been corrected (step S16). The reconstructed image is displayed on the image display unit 24. The user can change the correction mode as needed upon checking the displayed image (step S17).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray CT apparatus comprising:
   a plurality of X-ray tubes;
   a plurality of slit mechanisms which are respectively provided for said plurality of X-ray tubes and whose slit widths are adapted to be changed;
   a plurality of X-ray detectors which form pairs with said plurality of X-ray tubes, each said X-ray detector including a plurality of detection elements arrayed in a matrix form in a channel direction and a slice direction;
   a support mechanism which supports the X-ray tubes and the X-ray detectors so as to allow the X-ray tubes and the X-ray detectors to rotate about a rotation axis parallel to the slice direction;
   a correction unit which corrects projection data from each detection element located in an area which X-rays passing through the slit mechanism directly strike, based on data simultaneously collected from at least one detection element located outside the area and associated with the same channel in order to reduce a scattered radiation component originating from X-rays generated by an X-ray tube other than the X-ray tube forming the pair; and
   a reconstruction unit which reconstructs image data on the basis of the corrected data.

2. An apparatus according to claim 1, wherein the correction unit subtracts a value of the scattered radiation data from a value of the projection data.

3. An apparatus according to claim 1, wherein said correction unit subtracts an average of scattered radiation data from detection elements at two ends which are associated with the same channel from a value of the projection data.

4. An apparatus according to claim 1, wherein said correction unit subtracts scattered radiation data from one of detection elements at two ends which are associated with the same channel from a value of the projection data.

5. An apparatus according to claim 1, wherein said correction unit subtracts a value of scattered radiation data from adjacent detection elements associated with the same channel from a value of the projection data.

6. An apparatus according to claim 1, wherein an imaging axis which connects a focal point of the X-ray tube forming the pair to the center of the X-ray detector and an imaging axis which connects a focal point of the X-ray tube forming the other pair to the center of the X-ray detector intersect the rotation axis at right angles.

7. An X-ray CT apparatus comprising:
   a plurality of X-ray tubes;
   a plurality of slit mechanisms which are respectively provided for said plurality of X-ray tubes and whose slit widths are adapted to be changed;
   a plurality of X-ray detectors which form pairs with said plurality of X-ray tubes, each said X-ray detector including a plurality of detection elements arrayed in a matrix form in a channel direction and a slice direction;
   a support mechanism which supports the X-ray tubes and the X-ray detectors so as to allow the X-ray tubes and the X-ray detectors to rotate about a rotation axis parallel to the slice direction;
   a correction unit which corrects projection data from each detection element located in an area which X-rays passing through the slit mechanism directly strike, based on scattered radiation data simultaneously collected from at least one detection element located outside the area and associated with the same channel in order to reduce a scattered radiation component originating from X-rays generated by an X-ray tube other than the X-ray tube forming the pair; and
   a reconstruction unit which reconstructs image data on the basis of projection data which has not undergone the correction in a first mode of performing data acquisition by using a single pair of said plurality of pairs, and reconstructs image data based on projection data which has undergone the correction in a second mode of performing data acquisition by using said plurality of pairs.

8. An X-ray CT apparatus comprising:
   a plurality of X-ray tubes;
   a plurality of slit mechanisms which are respectively provided for said plurality of X-ray tubes and whose slit widths are adapted to be changed;
   a plurality of X-ray detectors which form pairs with said plurality of X-ray tubes, each said X-ray detector including a plurality of detection elements arrayed in a matrix form in a channel direction and a slice direction;
   a support mechanism which supports the X-ray tubes and the X-ray detectors so as to allow the X-ray tubes and the X-ray detectors to rotate about a rotation axis parallel to the slice direction;
   a setting support unit which supports setting of a scan condition by preparing a plurality of candidates associated with combinations of imaging slice thicknesses and imaging slice counts which correspond to an entire effective area of the X-ray detector in a first mode of performing data acquisition by using a single pair of said plurality of pairs, and by preparing a plurality of candidates corresponding to part of an effective area from which at least detection elements of the X-ray detector which are located on two end rows are excepted, in a second mode of performing data acquisition by using said plurality of pairs,
   a control unit which controls the slit mechanism in accordance with a combination of an imaging slice thickness and an imaging slice count which is selected in accordance with a user instruction;
   a correction unit which corrects data from each detection element located in part of the effective area which X-rays passing through the slit mechanism directly strike, by using data simultaneously collected from at least one detection element located outside the part and associated with the same channel in order to reduce a scattered radiation component originating from X-rays generated by an X-ray tube other than the X-ray tube forming the pair; and a reconstruction unit which reconstructs image data on the basis of data which has undergone the correction in the second mode, and reconstructs image data on the basis of data which has not undergone the correction in the first mode.

9. An X-ray CT apparatus comprising:

a plurality of X-ray tubes;

a plurality of slit mechanisms which are respectively provided for said plurality of X-ray tubes and whose slit widths are adapted to be changed;

a plurality of X-ray detectors which form pairs with said plurality of X-ray tubes, each said X-ray detector including a plurality of detection elements arrayed in a matrix form in a channel direction and a slice direction;

a support mechanism which supports the X-ray tubes and the X-ray detectors so as to allow the X-ray tubes and the X-ray detectors to rotate about a rotation axis parallel to the slice direction;

a control unit which controls the slit mechanism to apply X-rays to an entire effective area of the X-ray detector in a first mode of performing data acquisition by using a single pair of said plurality of pairs, and controls the slit mechanism to apply X-rays to part of an effective area of the X-ray detector from which at least two end rows are excepted, in a second mode of performing data acquisition by using said plurality of pairs;

a correction unit which corrects data from each detection element located in the part which X-rays passing through the slit mechanism directly strike, by using data collected simultaneously from at least one detection element located outside the area and associated with the same channel in order to reduce a scattered radiation component originating from X-rays generated by an X-ray tube other than the X-ray tube forming the pair; and a reconstruction unit which reconstructs image data on the basis of data which has undergone the correction in the second mode, and reconstructs image data on the basis of data which has not undergone the correction in the first mode.

* * * * *